United States Patent
DiPiano et al.

(10) Patent No.: US 7,591,808 B2
(45) Date of Patent: Sep. 22, 2009

(54) VAGINAL OR RECTAL APPLICATOR

(75) Inventors: Gerianne Tringali DiPiano, Malvern, PA (US); John Andrew Ziemniak, Gwynedd Valley, PA (US); Joel Martin Bartholomew, Danielsville, PA (US)

(73) Assignee: FemmePharma Holding Company, Inc., Wayne, PA (US)

( * ) Notice: Subject to any disclaimer, the term of this patent is extended or adjusted under 35 U.S.C. 154(b) by 342 days.

(21) Appl. No.: 10/759,695

(22) Filed: Jan. 16, 2004

(65) Prior Publication Data

US 2004/0260252 A1 Dec. 23, 2004

Related U.S. Application Data

(60) Provisional application No. 60/441,033, filed on Jan. 16, 2003.

(51) Int. Cl.
*A61M 31/00* (2006.01)
(52) U.S. Cl. ............... 604/275; 604/15; 604/91; 604/181
(58) Field of Classification Search ......... 604/275, 604/57, 91, 187, 59, 14–15, 181, 48, 514, 604/515, 73, 264, 278, 167
See application file for complete search history.

(56) References Cited

U.S. PATENT DOCUMENTS

| | | | | |
|---|---|---|---|---|
| 2,847,011 | A | * | 8/1958 | Jones .................. 604/232 |
| 3,667,465 | A | | 6/1972 | Voss |
| 3,780,735 | A | | 12/1973 | Crouter et al. |
| 3,850,173 | A | * | 11/1974 | Dash .................. 604/200 |
| 4,361,150 | A | | 11/1982 | Voss |
| 4,421,504 | A | * | 12/1983 | Kline .................. 604/12 |
| 4,620,534 | A | | 11/1986 | Zartman |
| 5,201,779 | A | | 4/1993 | Shiao |
| 5,213,566 | A | | 5/1993 | Weissenburger |
| 5,330,427 | A | | 7/1994 | Weissenburger |
| 5,462,740 | A | | 10/1995 | Evenstad et al. |
| 5,531,703 | A | | 7/1996 | Skwarek et al. |
| 5,662,601 | A | | 9/1997 | Snead |
| 5,681,279 | A | | 10/1997 | Roper et al. |
| 5,860,946 | A | | 1/1999 | Hofstätter |

(Continued)

FOREIGN PATENT DOCUMENTS

EP 0 263 976 4/1988

(Continued)

*Primary Examiner*—Nicholas D Lucchesi
*Assistant Examiner*—Quynh-Nhu H Vu
(74) *Attorney, Agent, or Firm*—Pabst Patent Group LLP

(57) ABSTRACT

Vaginal or rectal applicators for the delivery of a small volume of pharmaceutical preparation, i.e. less than 1 mL are disclosed herein. The delivery of a small volume of a pharmaceutical preparation allows for the transvaginal delivery of the preparation to the region of the upper vaginal vault or rectum for the treatment of diseases and disorders of the female urogenital system, cervix, uterus, ovaries, fallopian tubes and peritoneal cavity and the lower abdomen. The vaginal or rectal applicators contain four main parts, an applicator barrel, a plunger, a plunger tip, and an applicator cap. The applicator functions similar to a syringe. The applicator is filled with a pharmaceutical preparation with the plunger in the back position. The cap is attached to seal the pharmaceutical preparation in the applicator. To use the applicator, the cap is removed, the applicator is positioned, and the plunger is depressed.

9 Claims, 4 Drawing Sheets

U.S. PATENT DOCUMENTS

| | | | | |
|---|---|---|---|---|
| 6,027,471 | A * | 2/2000 | Fallon et al. | 604/59 |
| 6,224,573 | B1 * | 5/2001 | Yeager et al. | 604/181 |
| 6,547,467 | B2 * | 4/2003 | Quintero | 401/132 |

FOREIGN PATENT DOCUMENTS

| | | |
|---|---|---|
| EP | 0 633 033 | 1/1995 |
| GB | 1 248 636 | 10/1971 |

* cited by examiner

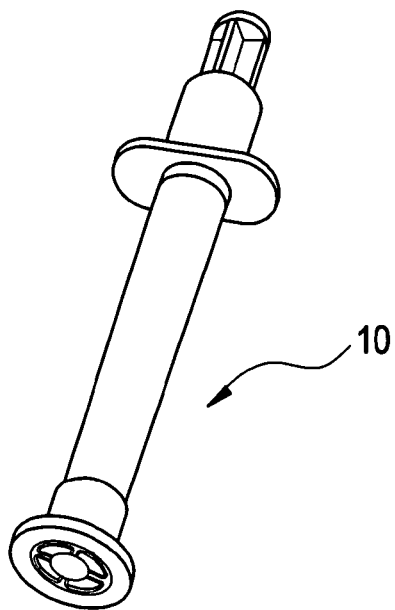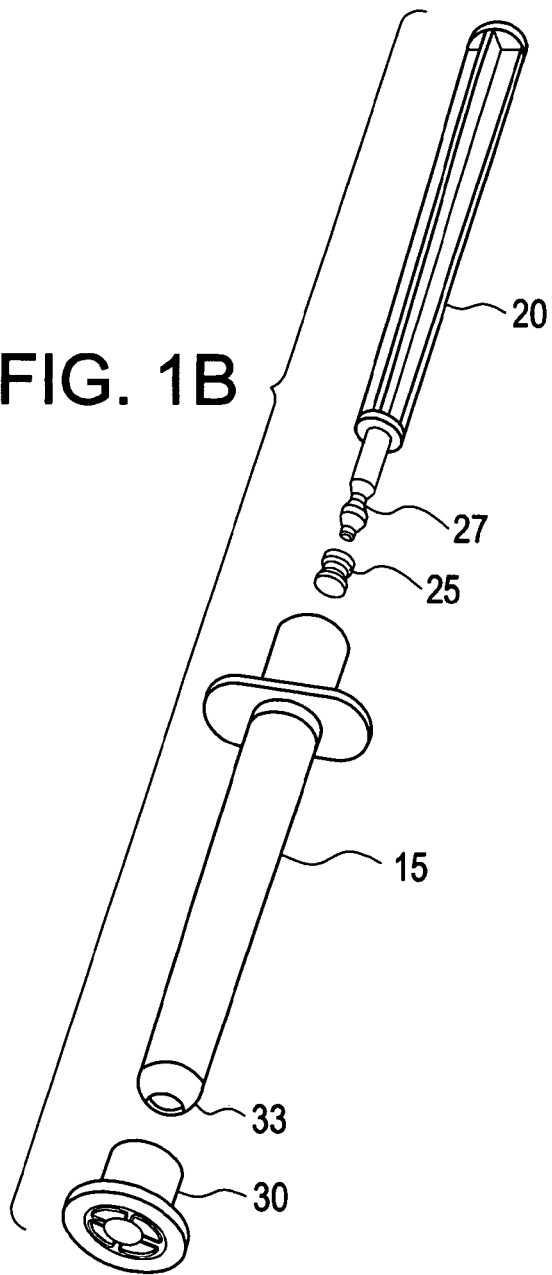

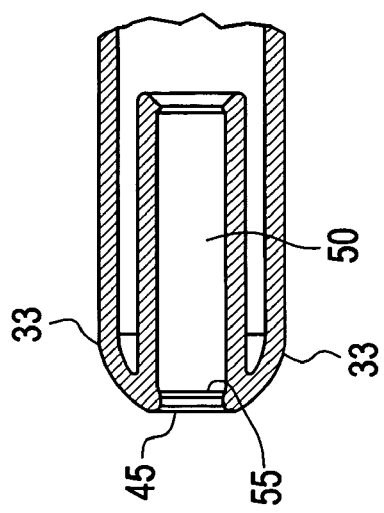
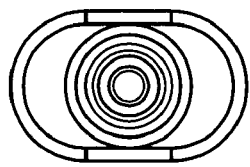
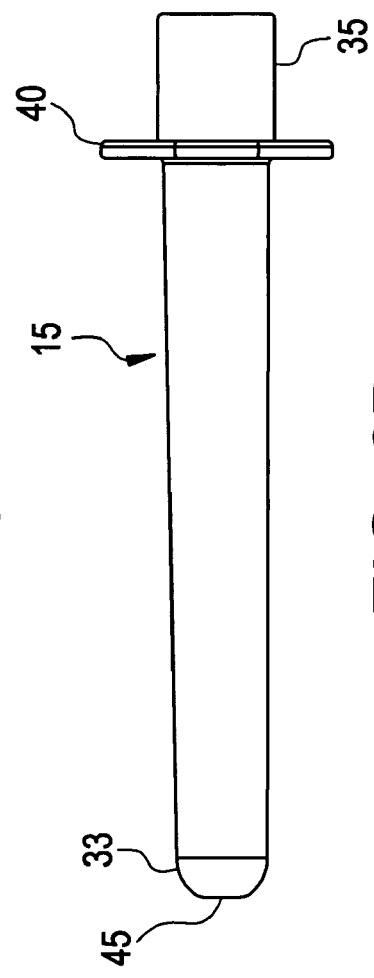
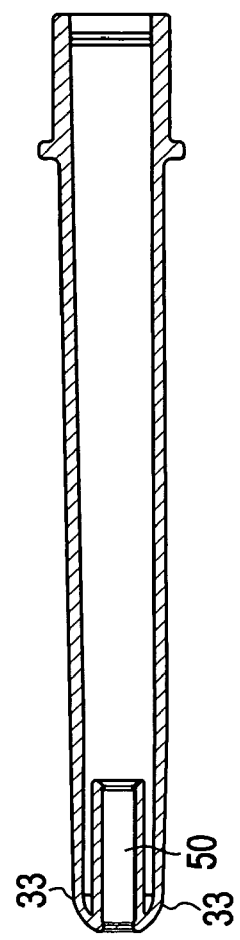

VAGINAL OR RECTAL APPLICATOR

CROSS-REFERENCE TO RELATED APPLICATIONS

This application claims benefit of U.S. Provisional Application No. 60/441,033, entitled "Vaginal Applicator", to Gerianne Tringali DiPiano, John Andrew Ziemniak, and Joel Martin Bartholomew, filed Jan. 16, 2003.

FIELD OF THE INVENTION

The present invention relates to devices for the transvaginal or rectal delivery of pharmaceutical preparations. In particular, the present invention is directed at vaginal and rectal applicators.

BACKGROUND OF THE INVENTION

Vaginal and rectal applicators have been used to dispense medications to treat vaginal diseases and disorders and diseases of the lower abdomen including the colon and rectum. They are sold both pre-filled and empty. For example, SCHERING-PLOUGH® Health Care Products, Memphis, Tenn., provides applicators for GYNE-LOTRIMIN®. Additionally, Ortho McNeil and Columbia Laboratories supply pre-filled applicators for dispensing a contraceptive gel and vaginal moisturizer, respectively. Generally, the vaginal applicator consists of an elongated small diameter cylindrical barrel and a plunger rod.

Vaginal and rectal applicators have traditionally been designed to deliver large volumes (e.g. greater than 1 mL) of pharmaceutical preparations. Vaginal applicators are typically used to delivery large volumes of drug for the treatment of diseases and disorders within the vagina, while rectal applicators have been used to treat diseases of the lower abdomen and bowel using large volumes of drug in the form of enemas, foams and suppositories. When such large volumes of drugs are delivered, they coat the entire vaginal epithelia, in the case of vaginal delivery, or anal canal, in the case of rectal delivery. The large volume of medication contained within the applicator poses aesthetic concerns and hygiene issues. Further, the amount of drug dispensed is often imprecise, which may result in over- or under-dosing.

Therefore it is an object of the invention to provide vaginal or rectal applicators that are able to precisely deliver small amounts of pharmaceutical compositions.

It is a further object of the invention to provide vaginal or rectal applicators for transvaginal or transrectal delivery of pharmaceutical compositions for regional administration.

BRIEF SUMMARY OF THE INVENTION

Vaginal or rectal applicators for the delivery of a small volume of pharmaceutical preparation, i.e. 1 mL or less, are disclosed herein. The delivery of a small volume of a pharmaceutical preparation allows for the transvaginal delivery of the preparation to the region of the upper vaginal vault or rectum for the treatment of diseases and disorders of the female urogenital system, cervix, uterus, ovaries, fallopian tubes and peritoneal cavity and the lower abdomen. The vaginal or rectal applicators contain four main parts: an applicator barrel, a plunger, a plunger tip, and an applicator cap. The applicator functions similar to a syringe. The applicator is breech-filled with a pharmaceutical preparation with the plunger in the back position. The applicator cap is attached to seal the pharmaceutical preparation in the applicator. To use the applicator, the cap is removed, the applicator is positioned, and the plunger is depressed.

BRIEF DESCRIPTION OF THE DRAWINGS

FIG. 1A is a side view of the vaginal or rectal applicator assembly.

FIG. 1B is a side view of the four main elements in the vaginal or rectal applicator assembly.

FIG. 2A is a side view of the applicator barrel.

FIG. 2B is a cross-sectional view of the applicator barrel.

FIG. 2C is an end view of the trailing end of the applicator barrel.

FIG. 2D is cross-sectional view of the tip of the applicator barrel.

DETAILED DESCRIPTION OF THE INVENTION

I. Vaginal or Rectal Applicator Assembly

Figure 3B:
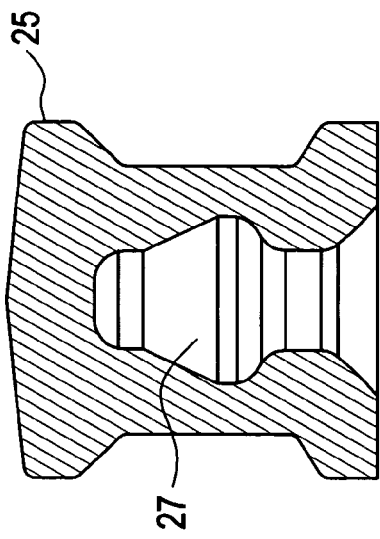
FIG. 3B is a cross-sectional view of the end of the plunger and the plunger tip.
Figure 3A:
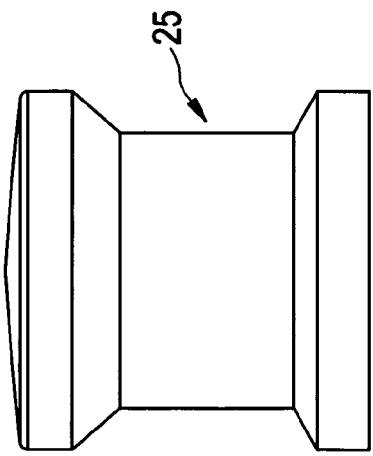
FIG. 3A is a side view of the plunger tip.
Figure 3C:
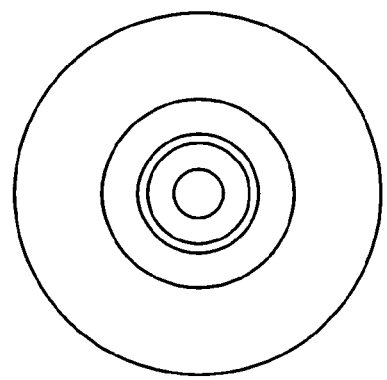
FIG. 3C is an aerial view of the end of the plunger.
Figure 4B:
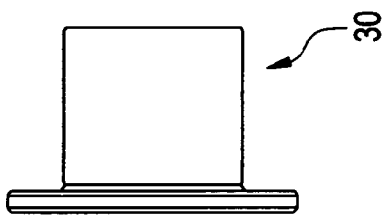
FIG. 4B is a side view of the applicator cap.
Figure 4C:
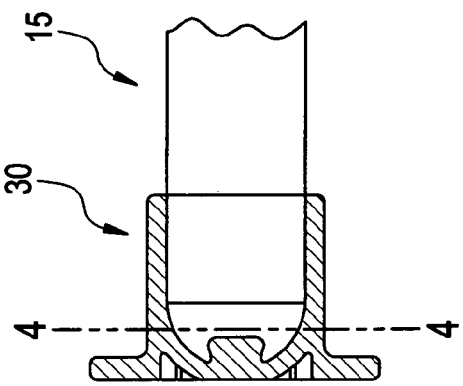
FIG. 4C is a cross-sectional view of the tip of the applicator barrel and the applicator cap.
Figure 4A:
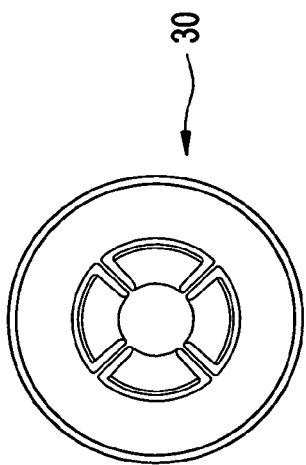
FIG. 4A is an end view of the applicator cap.
Figure 4D:
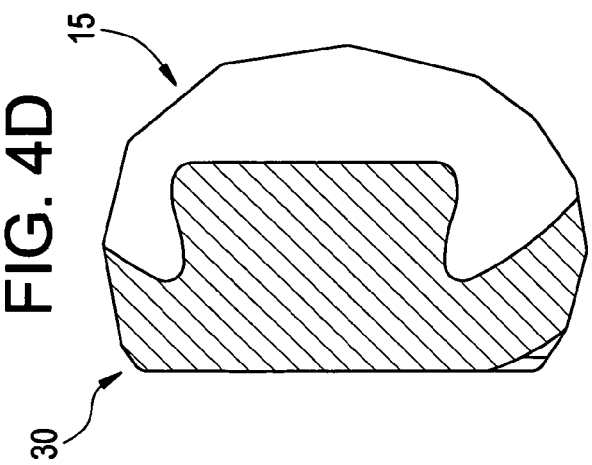
FIG. 4D is an enlarged cross-sectional view taken about lines 4-4 of FIG. 4C.

As shown in FIGS. 1A and 1B, the vaginal or rectal applicator (also referred to herein as the "vaginal/rectal applicator") assembly (10) contains an outer tubular member or applicator barrel (15) and an inner tubular member in the form of a plunger (20), which is insertable in telescoping relation to the applicator barrel (15) for the purpose of ejecting a pharmaceutical composition. The vaginal/rectal applicator assembly (10) contains a plunger tip (25), which is placed at the proximal end of the plunger (27), and forms an air-tight seal with the applicator barrel. The vaginal/rectal applicator assembly (10) also contains an applicator cap (30), which is placed at the tip of the applicator barrel (33) and forms an air-tight seal with the applicator barrel. The vaginal/rectal applicator assembly is formed from inert, hard, polymeric materials, such as polystyrene or polypropylene.

A. Applicator Barrel

As shown in FIG. 2A, the applicator barrel (15) is generally in the form of tube with an grip area (35) at its distal end, a flange (40) next to the grip area and an opening (45) at its rounded tip (33). FIGS. 2B and 2C show that the applicator barrel is a thin-walled tube. The cavity at the tip of the tube is the medication chamber (50). The diameter of the medication chamber (50) is smaller than the outer diameter of the applicator barrel. The medication chamber is large enough to contain a small volume of a pharmaceutical composition, which is 1 mL or less. In the preferred embodiment, the medication chamber is able to contain 200 µL of a pharmaceutical composition. Next to the medication chamber is a barrier (55), which prevents the plunger from pushing beyond the medication chamber. After the plunger is depressed, the barrier locks the plunger in place. In one embodiment, length from the flange to the tip of the applicator barrel is greater than or equal to 4 inches. Thus when the vaginal or rectal applicator device is inserted in a patient, the tip of the applicator barrel is inserted more than four inches into the vaginal cavity or is approximately four inches into the vaginal cavity. For rectal administration the length may be less than or equal to four inches. Alternatively, for some embodiments, a shorter applicator, with a length ranging from 1 to 2 inches, is useful. For example, for rectal administration of a pharmaceutical composition to the anal canal, a length of 1.5 to 2 inches is useful. Additionally, for applicators that are used to administer pharmaceutical compositions to children an applicator with a shorter length, such as approximately 1 inch, is useful.

The diameter and shape of the applicator is large enough to prevent penetration of the vaginal wall/cervix or rectum. The tip of the applicator is smooth, to ease insertion of the applicator. The length of the medication chamber (delivery stroke) is approximately 0.5 inches. This is a length where the user can distinguish the travel of the plunger from start to finish recognizing that the drug is delivered.

The flange (40) is sufficiently wide to prevent over-insertion of the applicator into the vagina and injury to the cervix. The applicator barrel has a grip area (35) behind the flange (40) to aid in insertion and handling of the device.

B. Plunger and Plunger Tip

As shown in FIG. 3B, the plunger tip (25) surrounds the proximal end of the plunger (27). The plunger tip is designed to stop at the end of the applicator barrel so that the user feels the stop and knows that the full dosage has been delivered. There is a space between the plunger and the applicator barrel to prevent excessive travel by the plunger. The plunger tip forms an air-tight seal with the applicator barrel. The design of the plunger tip ensures that all of the pharmaceutical formulation is pushed out of the medication chamber and delivered to the patient.

C. Applicator Cap

The applicator cap (30) has features designed to hinder insertion of the applicator into the vagina or the rectum with the cap attached (see FIGS. 4A-D). For example, the applicator cap (30) is wider than the applicator barrel (15) to prevent its insertion into the vagina. The applicator cap (30) forms an air-tight seal with the end of the applicator barrel (15) (see FIGS. 4C and 4D) to prevent contamination.

II. Method of Using the Vaginal or Rectal applicator Assembly

The applicator is breached filled, i.e. though the opening (45) at the tip (33) of the applicator barrel (15), with a pharmaceutical preparation with the plunger in the back position. A small volume of pharmaceutical preparation, i.e. 1 mL or less, is placed in the medication chamber. In a preferred embodiment, 0.2 mL of a pharmaceutical preparation is placed in the medication chamber. The pharmaceutical preparations may be in the form of a powder, gel, cream, lotion, suppository, ovule, tablet, or capsule. After filling the applicator, the applicator cap is attached to seal the pharmaceutical preparation in the applicator. To use the applicator, the cap is removed, the applicator is positioned in the patient's vagina or rectum, and the plunger is depressed.

III. Applications for the Vaginal or Rectal applicator Assembly

The vaginal applicator may be used to administer pharmaceutical formulations to the vagina or rectum. The pharmaceutical compositions may be delivered locally to the site of application or regionally to the surrounding area. As used herein, "locally" can refer to topical application generally to the mucosal or endometrial surfaces of the vagina. As used herein, "regionally" refers to reproductive organs and their surrounding environs, which include uterus, fallopian tube, peritoneal space, pelvic cul-de-sac, ovaries, perineum, abdominal; the rectovaginal region, and urinogenital tract, including bladder, urinary tract, and rectum. In the preferred embodiment, the drug formulations are delivered transvaginally to the region of the upper vaginal vault for the treatment of diseases and disorders of the female urogenital system, cervix, uterus, ovaries, fallopian tubes and peritoneal cavity.

In another embodiment, the formulations are administered locally within the vagina. Alternatively, the applicator can be used for rectal administration of pharmaceutical compositions, such as to deliver the drug to the colon or the anal canal.

The applicator can be used to deliver drugs for the treatment of diseases and disorders locally and regionally in the area of administration. For example, the vaginal applicator may be used to treat urinary incontinence or endometriosis. The rectal applicator may be used to deliver drug to the lower abdominal region to treat diseases such as colitis, ileitis, irritable bowel syndrome, Chron's Disease, or ulcerative colitis.

The term "drug" can refer to any pharmaceutically active substance capable of being administered in a particulate formulation, which achieves the desired effect. Drugs can be synthetic or natural organic compounds, proteins or peptides, oligonucleotides or nucleotides, or polysaccharides or sugars. Drugs may have any of a variety of activities, which may be inhibitory or stimulatory, such as antibiotic activity, antiviral activity, antifungal activity, steroidal activity, cytotoxic or anti-proliferative activity, anti-inflammatory activity, analgesic or anesthetic activity, or be useful as contrast or other diagnostic agents. A description of classes of drugs and species within each class can be found in Martindale, The Extra Pharmacopoeia, 31st Ed., The Pharmaceutical Press, London (1996) and Goodman and Gilman, The Pharmacological Basis of Therapeutics, (9th Ed., McGraw-Hill Publishing company (1996).

Examples of compounds with steroidal activity include progestins, estrogens, antiestrogens and antiprogestins.

In a preferred embodiment, the drug is danazole or gestrinone in a micro or nanoparticulate formulation. This can be achieved by milling of the drug or atomization of drug solution, for example, into a solvent extraction fluid, or other standard techniques. The danazole or gestrinone can be present as a complex with a cyclodextrin, for example, hydroxypropyl-$\beta$-cyclodextrin (HPB).

In another embodiment, the drug is a polysaccharide, preferably a sulfated polysaccharide. Examples of suitable sulfated polysaccharides include carageenan, dextran sulfate, heparin, and fucoidin.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A vaginal applicator for transvaginal drug delivery comprising
    (a) an applicator barrel, wherein the applicator barrel has a size and shape suitable for insertion into the vagina, preventing penetration of the vaginal wall or cervix, and delivering a pharmaceutical composition to the upper vaginal vault,
    wherein the applicator barrel comprises a medication chamber at the proximal end of the applicator, wherein the medication chamber has a smaller diameter than the inner diameter of the applicator barrel and defines a cavity within the applicator barrel having a volume of 1 mL or less, wherein there is a space between the applicator barrel and the medication chamber, wherein the medication chamber is designed to contain 1 mL or less of the pharmaceutical composition in a form selected from the group consisting of powder, gel, cream, and lotion, wherein the proximal end of the applicator contains an opening suitable for filling the medication chamber with the pharmaceutical composition and dispensing the pharmaceutical composition from the medication chamber, wherein the medication chamber comprises a dispensing end that cannot extend past the proximal end of the applicator barrel, and wherein the applicator barrel comprises a barrier proximal to the opening;

(b) a plunger, wherein the plunger is insertable in telescoping relation to the applicator barrel until the plunger reaches the barrier wherein the proximal end of the plunger comprises a plunger tip;

(c) a flange at the distal end of the applicator; and (d) an applicator cap, wherein the applicator cap is removable from the proximal end of the applicator barrel.

2. The vaginal or rectal applicator of claim 1, wherein the applicator cap has a diameter that is effective at preventing insertion of the vaginal applicator into a vagina when the applicator cap is attached to the applicator barrel.

3. The vaginal or rectal applicator of claim 1, wherein the applicator cap forms an air-tight seal with the applicator barrel.

4. The vaginal or rectal applicator of claim 1, wherein the plunger tip forms an air-tight seal with the applicator barrel.

5. The applicator of claim 1, wherein the applicator has a rounded tip at the proximal end of the applicator.

6. A method of transvaginal drug delivery comprising (1) breech filling a vaginal applicator with 1 mL or less of a pharmaceutical formulation, wherein the vaginal applicator comprises (a) an applicator barrel, wherein the applicator barrel has a size and shape suitable for insertion into the vagina, preventing penetration of the vaginal wall or cervix and delivering the pharmaceutical formulation to the upper vaginal vault, wherein the applicator barrel comprises a medication chamber at the proximal end of the applicator, wherein the medication chamber has a smaller diameter than the inner diameter of the applicator barrel and defines a cavity having a volume of 1 mL or less, wherein there is a space between the applicator barrel and the medication chamber, wherein the medication chamber comprises a dispensing end that cannot extend past the proximal end of the applicator barrel, and wherein the applicator barrel comprises a barrier proximal to the opening;

(b) a plunger, wherein the plunger is insertable in telescoping relation to the applicator barrel until the plunger reaches the barrier, wherein the proximal end of the plunger comprises a plunger tip; and (c) a flange at the distal end of the applicator;

(2) inserting the applicator barrel into a patient's vagina, wherein the pharmaceutical formulation is in a form selected from the group consisting of a powder, gel, cream, and lotion, and (3) depressing the plunger until it reaches the barrier to administer all of the pharmaceutical formulation to the patient's upper vaginal vault.

7. The method of claim 6, wherein the pharmaceutical formulation is in an amount effective to treat disorders and diseases of the female urogenital system, cervix, uterus, ovaries, fallopian tubes, and peritoneal cavity.

8. The method of claim 6, further comprising, after step (1) and prior to step (2), placing an applicator cap on the proximal end of the applicator barrel and then removing the applicator cap from the proximal end of the applicator barrel.

9. The method of claim 6, wherein the applicator has a rounded tip at the proximal end of the applicator.

* * * * *